United States Patent
Conner et al.

(10) Patent No.: US 7,396,850 B2
(45) Date of Patent: Jul. 8, 2008

(54) PYRAZOLE DERIVATIVE AS PPAR MODULATOR

(75) Inventors: Scott Eugene Conner, Indianapolis, IN (US); Nathan Bryan Mantlo, Brownsburg, IN (US); Daniel Ray Mayhugh, Carmel, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 575 days.

(21) Appl. No.: 10/537,282

(22) PCT Filed: Dec. 31, 2003

(86) PCT No.: PCT/US03/39117

§ 371 (c)(1),
(2), (4) Date: May 31, 2005

(87) PCT Pub. No.: WO2004/063165

PCT Pub. Date: Jul. 29, 2004

(65) Prior Publication Data

US 2007/0043220 A1    Feb. 22, 2007

Related U.S. Application Data

(60) Provisional application No. 60/438,563, filed on Jan. 6, 2003.

(51) Int. Cl.
*A61K 31/415* (2006.01)
*C07D 231/10* (2006.01)

(52) U.S. Cl. ............... 514/406; 548/356.1; 548/373.1; 548/376.1; 514/403; 424/1.37

(58) Field of Classification Search ............. 548/356.1, 548/373.1, 376.1; 514/403, 406; 424/1.37
See application file for complete search history.

(56) References Cited

U.S. PATENT DOCUMENTS

| 6,458,744 B2 * | 10/2002 | Wu et al. ............... 504/105 |
| 2006/0148858 A1 | 7/2006 | Takeda |
| 2006/0241157 A1 | 10/2006 | Lilly |

FOREIGN PATENT DOCUMENTS

| EP | 0442448 A2 | 12/1991 |
| EP | 0442448 A3 | 12/1991 |
| JP | 11130753 | 5/1999 |
| WO | WO 01/16120 A1 | 3/2001 |
| WO | WO 02/100403 A1 | 12/2002 |

* cited by examiner

*Primary Examiner*—Golam M. M. Shameem
(74) *Attorney, Agent, or Firm*—MaCharri Vorndran-Jones

(57) ABSTRACT

The present invention is directed to a compound, {2-Methyl-4-[3-methyl-1-(4-trifluoromethyl-phenyl)-1H-pyrazol-4-yl-methylsulfanyl]-phenoxy}-acetic acid and pharmaceutical uses thereof.

9 Claims, No Drawings

PYRAZOLE DERIVATIVE AS PPAR MODULATOR

This application is a United States national phase entry, pursuant to 35 U.S.C. 371, of PCT/US2003/039117, filed on Dec. 31, 2003, which claims the benefit of United States provisional patent application Ser. No. 60/438,563, filed Jan. 6, 2003.

Information disclosed and/or claimed in this patent application has been generated pursuant to a joint research agreement among Eli Lilly and Company and Ligand Pharmaceuticals, Inc.

BACKGROUND OF THE INVENTION

Peroxisome Proliferator Activated Receptors (PPARs) are members of the nuclear hormone receptor superfamily, a large and diverse group of proteins that mediate ligand-dependent transcriptional activation and repression. Three subtypes of PPARs have been isolated: PPARα, PPARγ and PPARδ.

The expression profile of each isoform differs significantly from the others, whereby PPARα is expressed primarily, but not exclusively in liver; PPARγ is expressed primarily in adipose tissue; and PPARδ is expressed ubiquitously. Studies of the individual PPAR isoforms and ligands have revealed their regulation of processes involved in insulin resistance and diabetes, as well as lipid disorders, such as hyperlipidemia and dyslipidemia. PPARγ agonists, such as pioglitazone, can be useful in the treatment of non-insulin dependent diabetes mellitus. Such PPARγ agonists are associated with insulin sensitization.

PPARα agonists, such as fenofibrate, can be useful in the treatment of hyperlipidemia. Although clinical evidence is not available to reveal the utility of PPARδ agonists in humans, several preclinical studies suggest that PPARδ agonists can be useful in the treatment of diabetes and lipid disorders.

The prevalence of the conditions that comprise Metabolic Syndrome (obesity, insulin resistance, hyperlipidemia, hypertension and atherosclerosis) continues to increase. New pharmaceutical agents are needed to address the unmet clinical needs of patients.

PPARδ agonists have been suggested as a potential treatment for use in regulating many of the parameters associated with Metabolic Syndrome and Atherosclerosis. For example, in obese, non-diabetic rhesus monkeys, a PPARδ agonist reduced circulating triglycerides and LDL, decreased basal insulin levels and increased HDL (Oliver, W. R., et al.; Proc Natl Acad Sci 98:5306-5311; 2001). The insulin sensitization observed with the use of a PPARδ agonist is thought to be in part due to decreased myocellular lipids (Dressel, U., et al.; Mol Endocrinol 17:2477-2493; 2003).

Further, atherosclerosis is considered to be a disease consequence of dyslipidemia and may be associated with inflammatory disease. C-reactive protein (CRP) production is part of the acute-phase response to most forms of inflammation, infection and tissue damage. It is measured diagnostically as a marker of low-grade inflammation. Plasma CRP levels of greater than 3 mg/L have been considered predictive of high risk for coronary artery disease (J. Clin. Invest 111: 1085-1812; 2003).

PPARδ agonists are believed to mediate anti-inflammatory effects. Indeed, treatment of LPS-stimulated macrophages with a PPARδ agonist has been observed to reduce the expression of iNOS, IL12, and IL-6 (Welch, J. S., et al.; Proc Natl Acad Sci 100:6712-67172003).

SUMMARY OF THE INVENTION

The present invention is directed to the compound of the Formula I:

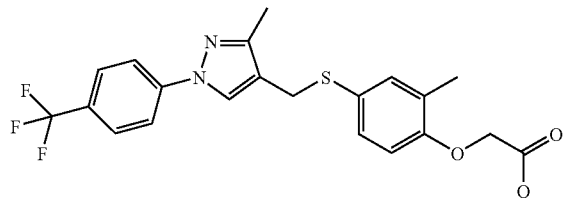

and pharmaceutically acceptable salts, solvates and hydrates thereof.

In one embodiment, the present invention also relates to pharmaceutical compositions comprising a compound of Formula I, or a pharmaceutically acceptable salt, solvate, or hydrate thereof, and a pharmaceutically acceptable carrier.

In another embodiment, the present invention relates to a method of selectively modulating a PPAR delta and/or PPAR alpha receptor(s) by contacting the receptor with a compound of Formula I, or a pharmaceutically acceptable salt, solvate, or hydrate thereof.

In a further embodiment, the present invention relates to a method of making a compound represented by Structural Formula I.

The compound of the present invention is believed to be effective in treating and preventing Metabolic Syndrome, Type II diabetes, hyperglycemia, hyperlipidemia, obesity, coagaulopathy, hypertension, atherosclerosis, and/or other disorders related to Metabolic Syndrome and cardiovascular diseases. Further, compounds of this invention can be useful for lowering fibrinogen, increasing HDL levels, treating renal disease, controlling desirable weight, treating demyelinating diseases, treating inflammatory disease including rheumatoid arthritis, asthma, Crohne's disease and psorias, treating certain viral infections, and treating liver disease. It is believed that the compound of this invention may prevent and/or reverse the clinical effects of atherosclerosis and can minimize the likelihood of future adverse cardiac events. In addition, the pyrazole compound can be associated with fewer clinical side effects and may have clinically significant benefits when compared to compounds currently used to treat such conditions.

DETAILED DESCRIPTION OF THE INVENTION

The terms used to describe the instant invention have the following meanings. Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof. "Pharmaceutically-acceptable salt" refers to salts of the compounds of the Structural Formula I which are considered to be acceptable for clinical and/or veterinary use. Typical pharmaceutically acceptable salts include those salts prepared by reaction of the compounds of the present invention with a mineral or organic acid or an organic or inorganic base. Such salts are known as acid addition salts and base addition salts, respectively. It will be recognized that the particular counterion forming a part of any salt of this invention is not of a critical nature, so long as the salt as a whole is pharmaceutically acceptable and as long as the counterion does not contribute undesired qualities to the salt as a whole. These salts may be prepared by methods known to the skilled artisan.

The term, "active ingredient" means the compound described by Structural Formula I as well as any salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well-known and readily available ingredients.

"Preventing" refers to reducing the likelihood that the recipient will incur or develop any of the pathological conditions described herein. The term "preventing" is particularly applicable to a patient that is susceptible to the particular patholical condition.

"Treating" refers to mediating a disease or condition and preventing, reversing the clinical effects of the disease, or mitigating, its further progression or ameliorate the symptoms associated with the disease or condition.

PPARδ has been proposed to associate with and dissociate from selective co-repressors (BCL-6) that control basal and stimulated anti-inflammatory activities (Lee, C-H., et al.; Science 302:453-457 2003). PPARδ agonists are thought to be useful to attenuate other inflammatory conditions such as inflammation of the joints and connective tissue as occurs in rheumatoid arthritis, related autoimmune diseases, osteroarthritis, as well as myriad other inflammatory diseases, Crohne's disease, and psoriasis.

"Pharmaceutically-effective amount" means that amount of active ingredient, which will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition.

Generally, the effective amount of a Compound of Formula I will be between 0.02 through 5000 mg per day. Preferably the effective amount is between 1 through 1,500 mg per day. Preferably the dosage is from 1 through 1,000 mg per day. Most preferabley the dose is from 1 through 100 mg per day.

The desired dose may be presented in a single dose or as divided doses administered at appropriate intervals. Dosages that are administered less frequently than daily may be effective or desired for a particular indication or patient. It may be desired that the patient is diagnosed with Metabolic Syndrome or Atherosclerosis. It is generally preferred that the patient is diagnosed by a health care provider as being in need of such treatment as claimed herein.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compound and compositions of the present invention are useful for the treatment and/or prophylaxis of cardiovascular disease, for raising serum HDL cholesterol levels, for lowering serum triglyceride levels and/or for lower serum LDL cholesterol levels. Elevated triglyceride and LDL levels, and low HDL levels, are risk factors for the development of heart disease, stroke, and circulatory system disorders and diseases.

The compound and compositions of the present invention can also useful for treating and/or preventing obesity. The compound may also be useful in the treatment of Metabolic Syndrome and its associated conditions.

Further, the compound and compositions of the present invention may reduce the incidence of undesired cardiac events in patients. The physician of ordinary skill will know how to identify humans who will benefit from administration of the compounds and compositions of the present invention.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more.

When used herein Metabolic Syndrome includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis. In addition, the methods and treatments mentioned herein include the above and encompass the treatment and/or prophylaxis of any one of or any combination of the following inflammatory and autoimmune diseases: adult respritory distress syndrome, rheumatoid arthritis, demyelinating disease, Chrohne's disease, asthma, systemic lupus erythematosus, psoriasis, and bursitis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I, a stereoisomer, salt, solvate and/or hydrate thereof ("Active Igredient") and one or more additional active agents, as well as administration of a compound of Formula I and each active agent in its own separate pharmaceutical dosage formulation. For example, a Compound of Formula I and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times; combination therapy is understood to include all these regimens.

An example of combination treatment or prevention of atherosclerosis may be wherein the Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agents.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredient of the present invention, have valuable pharmacological properties and can be used in pharmaceutical compositions containing a therapeutically effective amount of the Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient, calculated to produce the desired therapeutic effect, in association with one or more pharmaceutically acceptable excipients. The quantity of the Active Ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Preferably, the compounds of the present invention are administered in a single daily dose, or the total daily dose may be administered in divided doses, two, three, or more times per day. It may be preferred to administer the Active Ingredient intermittently, i.e., less frequently than daily. When administered less frequently than daily, it may be preferred that the dosing interval is consistent. Thus, it may be preferable to dose, for example, every other day, weekly, twice monthly, monthly, and the like. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the invention can also be administered in a targeted drug delivery system, such as, for example, in a liposome coated with endothelial cell-specific antibody. Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

SYNTHESIS

Compounds of the present invention have been formed as specifically described in the examples. Further, many compounds are prepared as more generally using a) alkylation of phenol/thiophenol with a halide, b) a Mitsunobu protocol (O. Mitsunobu; 1981 Synthesis, p1); c) and other methods known to the skilled artisan. Alternative synthesis methods may also be effective and known to the skilled artisan.

For example, an intermediate like A is alkylated with an alkylating agent B in the presence of a base (e.g., K2CO3, Cs2CO3 etc.). Hydrolysis in the presence of aqueous NaOH or LiOH gave the acid product.

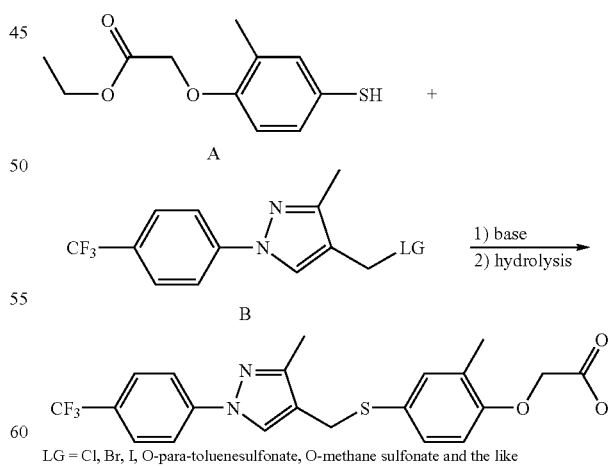

LG = Cl, Br, I, O-para-toluenesulfonate, O-methane sulfonate and the like

Alternatively, an intermediate like A is coupled with an alcohol C under Mitsunobu reaction condition (DEAD/PPh3, ADDP/PBu3 etc.). Hydrolysis in the presence of aqueous NaOH or LiOH gave the acid product:

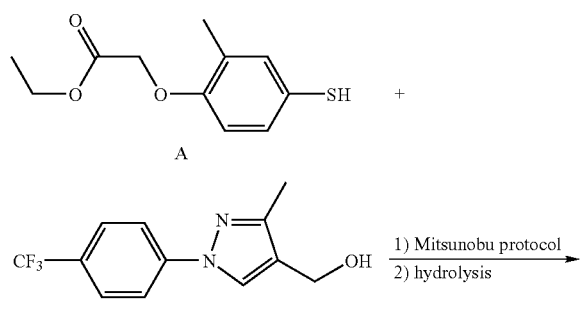

Thioether could also be prepared by a ZnI2 mediated thioether formation reaction as shown below:

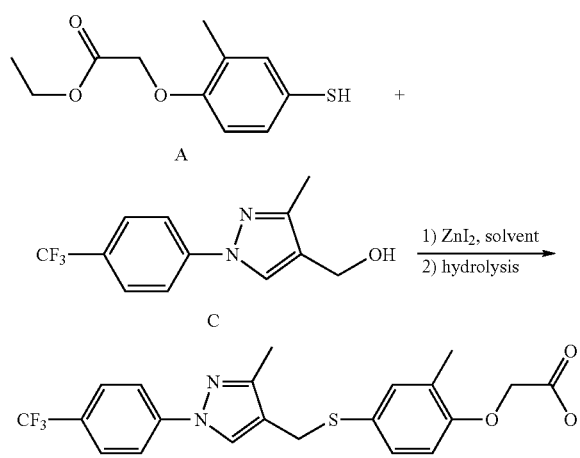

Intermediates B and C can be made in one of the following methods. Coupling reaction between pyrazole and aryl boronic acid or Aryl halide in the presence of copper gave the 1-arylpyrazole:

Scheme 1

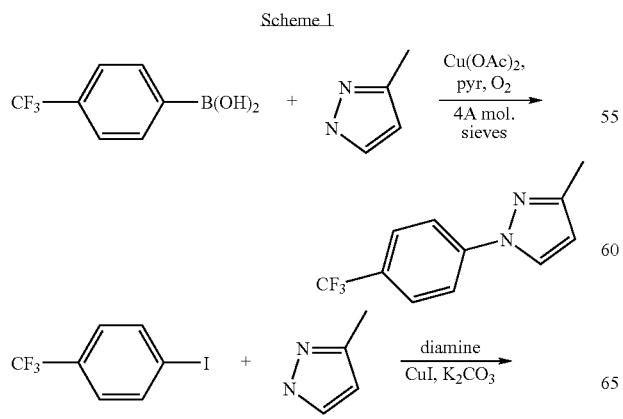

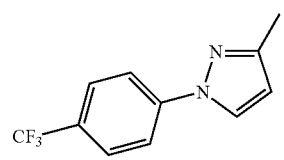

Formylation under Vilsmeier-Haack reaction condition of the 1-arylpyrazole gave the 4-formyl pyrazole, sodium borohydride reduction afforded the primary alcohol.

Scheme 2

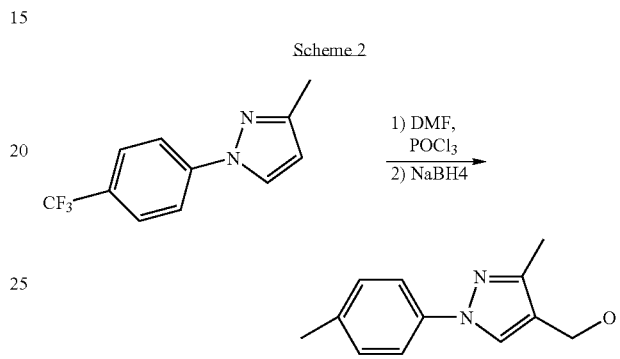

Alternatively, the pyrazole intermediates can be made by the following method starting from β-ketoesters:

Scheme 3

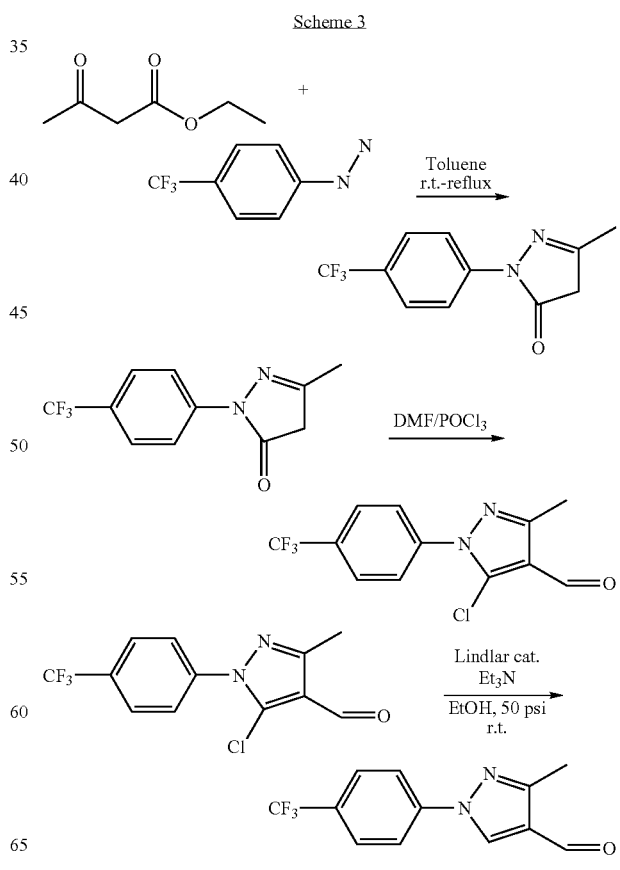

EXEMPLIFICATION

The Examples provided herein are illustrative of the invention claimed herein and are not intended to limit the scope of the claimed invention in any way.

Instrumental Analysis

Infrared spectra are recorded on a Perkin-Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). High resolution mass spectra are obtained on VG ZAB 3F or VG 70 SE spectrometers.

Analytical thin layer chromatography is performed on EM Reagent 0.25 mm silica gel 60-F plates. Visualization is accomplished with UV light.

Preparation 1

3-Methyl-1-(4-trifluoromethyl-phenyl)-1H-pyrazole-4-carbaldehyde

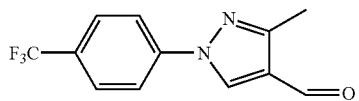

This aldehyde intermediate can be made by the following two methods.

Method I

Step A

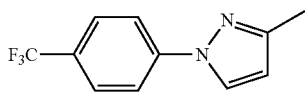

The intermediate can be obtained from two separate methods.

Method 1

3-Methyl-1-(4-trifluoromethyl-phenyl)-1H-pyrazole

To a solution of 4-(trifluoromethyl)phenylboronic acid (5.04 g, 26.5 mmol), 3-methylpyrazole (1.1 ml, 13.2 mmol), and pyridine (2.1 ml, 26.5 mmol) in dichloromethane (160 ml) is added copper(II) acetate (3.61 g, 19.9 mmol) and 4A molecular sieves (10.0 g). The suspension is stirred at ambient temperature in the open air for 48 hours, then filtered through Celite and concentrated in vacuo to a crude solid. Purification by silica flash chromatography (40:1 hexanes: ethyl acetate to 10:1 hexanes:ethyl acetate) yields the title compound as a white solid. MS: m/z (M+1) 227

Method 2

3-Methyl-1-(4-trifluoromethyl-phenyl)-1H-pyrazole

A mixture of 4-iodobenzotrifluoride (246 g, 0.904 mol), 3-methylpyrazole (90 g, 1.09 mol) and potassium carbonate (254 g, 1.83 mol) in 1,4-dioxane (1 L) under N$_2$ is treated with cupric iodide (1.75 g, 9.1 mmol) and trans-1,2-cyclohexanediamine (7.5 ml, 62.4 mmol) and heated at 110° C. for 30 hours. The mixture is cooled and diluted with water (1.5 L) and ethyl acetate (1.5 L). The organic layer is washed with water (1 L) and concentrated to an oil. Purification by silica flash chromatography (4:1 hexanes:ethyl acetate) yields the title compound as a white solid. MS: m/z (M+1) 227

Step B

3-Methyl-1-(4-trifluoromethyl-phenyl)-1H-pyrazole-4-carbaldehyde

To a solution of 3-Methyl-1-(4-trifluoromethyl-phenyl)-1H-pyrazole (1.88 g, 8.31 mmol) in DMF (8.0 ml) heated at 90° C. is carefully added phosphorous oxychloride (1.0 ml, 10.8 mmol) and the resulting mixture heated at 90° C. for 7 hours. Additional phosphorous oxychloride (0.75 ml, 8.0 mmol) is added and the mixture heated for an additional 2 hours. The mixture is cooled at 0° C., then carefully treated with cold water (75 ml). After dilution with diethyl ether. (40 ml) to dissolve solids, the mixture is adjusted to pH 3 with 5 N NaOH. The aqueous layer is extracted with diethyl ether (2×25 ml), the organic extracts then combined and washed with water, brine, dried (Na$_2$SO$_4$) and concentrated to a crude solid. Purification by silica flash chromatography (20:1 hexanes:ethyl acetate to 5:1 hexanes:ethyl acetate) provided the title compound as a white solid. MS: m/z (M+1) 255.

Method II

Step A

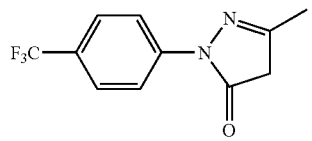

To a solution of the Trifluoromethylphenyl Hydrazine (60.4 g, 0.34 moles) and toluene (250.0 mL) at room temperature is added ethylacetoacetate (48.09 mL, 0.38 m). Reaction solution is then stirred overnight at r.t. for 12 hrs (N.B. reaction generally becomes hazy after an hour of stirring). Heated at reflux with continuous azeotropic removal of water and volatile organic solvents for another 12 hrs (note: the volume of toluene removed during azeotrope should be replaced during the course of the reaction). Reaction is monitored by TLC (1:1 EtoAc/Heptane). After the reaction is deemed to be complete, heptane (500.0 mL) is added to the hot solution. An off tan precipitate is observed upon equilibration to ambient temperature. The tan precipitate is filtered and the cake washed with heptane (75.0 mL), dried in an oven at 50° C. overnight (mass=75.39 g; 90% wt. Yield; $^1$H (CDCl₃+DMSOd₆) δ 1.82 (s, 3H), 3.16 (s, 2H), 7.22-7.25 (d, 2H, J=8.8 Hz), 7.57-7.59 (d, 1H, J=8.8 Hz), 7.66-7.68 (d, 1H, J=8.5 Hz).

Step B

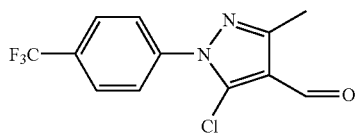

To DMF (44.56 mL, 0.57 m) at 10° C. is added POCl₃ (52.68 mL, 0.57 m) over a period of 30 minutes (caution solution solidifies after addition). To this solid is then added the pyrazolone (70.0 g, 0.28 m). Slowly heated mixture until dissolution is observed at 75-80° C. (To aid the dissolution, an extra 40 mL of DMF is added). The dark reaction solution is then heated at 90-100° C. for 18 hrs, after which an additional POCl₃ (52.6 mL) is added (reaction is monitored by TLC 1:1 EtoAc/Heptane). Heating is continued for another 6 hrs before the reaction mixture is very carefully reversed quenched into crushed ice over a period of 2 hrs. (Extreme caution: quenching is quite exothermic and should be done very carefully. Possible induction period can be observed during quenching of excess POCl₃). A dark brown precipitate is observed after quenching. On equilibration to r.t., the precipitate is extracted with CH₂Cl₂ (500.0 mL), washed with 2N NaOH (2×500 ml), treated with Darco and anh. MgSO₄. Subsequent filtration over hyflo and concentration at reduced pressure on the rotovap afforded a tan precipitate (mass=72.0 g). The purity of the precipitate can be upgraded by dissolving it in a hot EtoAc (200 ml), followed by a quick plug over silica gel. Concentration of the filtrate on the rotovap affords a tan solid (mass=68.4 g; 82% wt.Yield; ¹H (CDCl₃) δ 2.54 (s, 3H), 7.72-7.81 (m, 4H), 9.99 (s, 1H, C$\underline{H}$O).

Step C

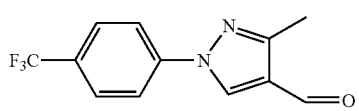

To Chloro/formyl starting material (520 mg, 1.8 mm) dissolved in EtOH (20.0 mL) is added Et₃N (0.5 mL) and Lindlar catalyst (0.05 g). The mixture is then hydrogenated at r.t (50 psi). After 2.5 hrs, ¹H nmr of an aliquot after a brief work up indicated product with no observable starting material. Reaction mixture is the filtered over hyflo, concentrated to a solid. To the solid is added CH₂Cl₂ (40.0 mL) and 1NHCl (20.0 mL) with stirring. Subsequent separation of lower organic layer, drying and concentrating on the rotovap afforded a tan precipitate (mass=455 mg; 100% wt.yield; ¹H (CDCl₃) δ 2.57 (s, 3H), 7.71-7.74 (d, 2H, J=8.4 Hz), 7.82-7.85 (d, 2H, J=8.5 Hz), 8.43 (s, 1H), 10.00 (s, 1H, C$\underline{H}$O).

Preparation 2

[3-Methyl-1-(4-trifluoromethyl-phenyl)-1H-pyrazol-4-yl]-methanol

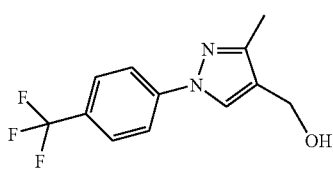

To a chilled (0° C.) suspension of 3-Methyl-1-(4-trifluoromethyl-phenyl)-1H-pyrazole-4-carbaldehyde (350 mg, 1.37 mmol) in ethanol (6 ml) is added sodium borohydride (52 mg, 1.37 mmol) portionwise over two minutes. The reaction mixture is removed from the cold bath and stirred for one hour. After quenching with water (25 ml), the reaction mixture is extracted with diethyl ether (3×15 ml). The combined organic extracts are washed with water, brine, then dried (Na₂SO₄) and concentrated to provide the title compound as a white solid. MS: m/z (M+1) 257.

Preparation 3

4-Chloromethyl-3-methyl-1-(4-trifluoromethyl-phenyl)-1H-pyrazole

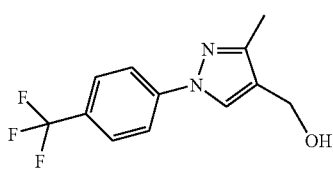

A solution of (3-methyl-1-(4-trifluoromethyl-phenyl)-1H-pyrazol-4-yl)-methanol (3.72 mmol) and triethyl amine (1.04 mL, 7.4 mmol) in methylene chloride (16 mL) is cooled to 0° C., then MeSO2Cl (0.46 mL, 5.95 mmol) is added dropwise. After 4 hrs, the reaction mixture is diluted with methylene chloride and washed with sodium bicarbonate, water and brine, dried over sodium sulfate. Concentration yields the crude title compound, which is used for the next step without further purification.

Preparation 4

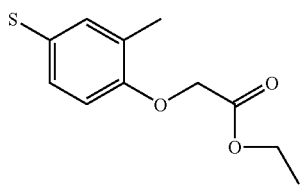

Step A (4-Chlorosulfonyl-2-methyl-phenoxy)-acetic acid ethyl ester

Chlorosulfonic acid (539.92 g, 308 mL, 4.63 mol) was cooled to 0° C. and the ethyl(2-methylphenoxyacetate) (300 g, 1.54 mol) was added dropwise. The internal temperature never rose above 8 oC. Stir approximately 30 minutes more cold, then remove the bath and stir an additional 2 hours. The mixture was poured into ice water, forming a white solid, which was filtered and washed with ice water. The solid was dried under vacuum overnight (40° C.) to produce 376 g (83%) of a white solid.

NMR (CDCl$_3$) δ 7.85 (d, J=10.0, 2.7 Hz, 2H), 6.8 (d, J=2 Hz, 1H), 4.77 (s, 2H), 4.29 (q, J=7.1 Hz, 2H), 2.37 (s, 3H), 1.31 (t, J=7.1 Hz, 3H).

Step B (4-Mercapto-2-methyl-phenoxy)-acetic acid ethyl ester

This step can be carried out by the following two procedures:

Method 1

To a stirred suspension of Zn powder (10 μm, 78.16 g, 1.2 mol) and dichlorodimethyl silane (154.30 g, 145.02 mL, 1.2 mol) in 500 mL of dichloroethane was added a solution of (4-Chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition was at a rate so as to maintain the internal temperature at ~52° C., cooling with chilled water as necessary. After addition was complete, the mixture was heated at 75° C. for 1 hour. It was then cooled to room temperature, filtered and concentrated iv. Add MTBE, wash twice with saturated LiCl solution, concentrate iv again. Take up the residue in CH$_3$CN, wash with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yielded 61 g (79%) of a clear, colorless oil.

NMR (DMSO-d$_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Method 2

(4-Chlorosulfonyl-2-methyl-phenoxy)-acetic acid ethyl ester (28.42 g, 97.08 mmol) was refluxed with Sn powder (60 g) in EtOH (125 mL) and dioxane/HCl (125 mL). After 3.5 hours, TLC showed reaction complete (25% EtOAc/hexane, UV). Cool to room temperature, add ~300 mL of ice and extract with CH$_2$Cl$_2$ (3×). Dry the organic phase (MgSO$_4$), filter and concentrate to yield (4-Mercapto-2-methyl-phenoxy)-acetic acid ethyl ester

EXAMPLE

{2-Methyl-4-[3-methyl-1-(4-trifluoromethyl-phenyl)-1H-pyrazol-4-ylmethylsulfanyl]-phenoxy}-acetic acid

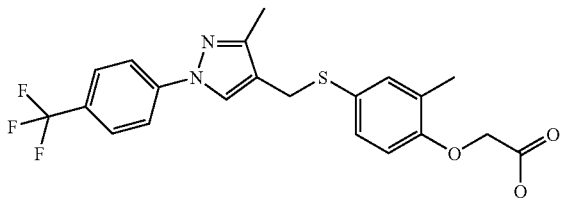

Step A

{2-Methyl-4-[3-methyl-1-(4-trifluoromethyl-phenyl)-1H-pyrazol-4-ylmethylsulfanyl]-phenoxy}-acetic acid ethyl ester

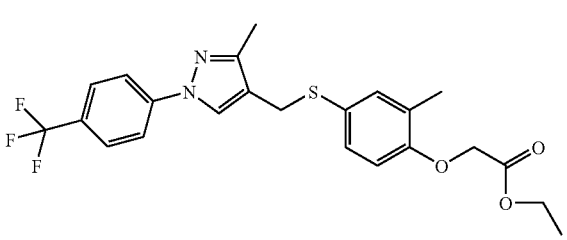

This compound can be made by the following three methods:

Method 1 (Alkylation Route)

General Procedure

To a solution of (4-Mercapto-2-methyl-phenoxy)-acetic acid ethyl ester (0.50 mmol) and 4-Chloromethyl-3-methyl-1-(4-trifluoromethyl-phenyl)-1H-pyrazole (167 mg, 0.61 mmol) in acetonitrile (1.5 ml) was added cesium carbonate (260 mg, 0.80 mmol) and the resulting suspension stirred at ambient temperature for 18 hours. Filtration of the mixture and concentration of the filtrate gave a solid which was purified by silica chromatography (15:1 hexanes:ethyl acetate to 5:1 hexanes-ethyl acetate) to provide {2-Methyl-4-[3-methyl-1-(4-trifluoromethyl-phenyl)-1H-pyrazol-4-ylmethylsulfanyl]-phenoxy}-acetic acid ethyl ester.

Method 2 (Mitsunobu Protocol)

General Procedure

To a cooled (0° C.) solution of [3-Methyl-1-(4-trifluoromethyl-phenyl)-1H-pyrazol-4-yl]-methanol (135 mg, 0.52 mmol) and (4-Mercapto-2-methyl-phenoxy)-acetic acid ethyl ester (0.63 mmol) in tetrahydrofuran (5.0 ml) was added tri-n-butylphosphine (0.195 ml, 0.78 mmol) followed by addition of 1,1'-(azodicarbonyl)dipiperidine (197 mg, 0.78 mmol) portion-wise over 3 minutes. The mixture was stirred at 0° C. for 10 minutes, then removed from the cold bath and stirred for 18 hours. The mixture was diluted with hexanes (10 ml), filtered to remove insolubles, and the filtrate concentrated to an oil which was purified by silica flash chromatography (35:1 hexanes:ethyl acetate to 5:1 hexanes:ethyl acetate) to provide {2-Methyl-4-[3-methyl-1-(4-trifluoromethyl-phenyl)-1H-pyrazol-4-ylmethylsulfanyl]-phenoxy}-acetic acid ethyl ester.

Method 3 (ZnI2 Mediated Thioether Formation)

General Procedure

Zinc iodide (105 mg, 0.33 mmol) was added to a solution of [3-Methyl-1-(4-trifluoromethyl-phenyl)-1H-pyrazol-4-yl]-methanol (0.65 mmol) and (4-Mercapto-2-methyl-phenoxy)-acetic acid ethyl ester (176 mg, 0.78 mmol) in 1,2-dichloroethane (1 ml) and the solution stirred at ambient temperature for 1 hour. The mixture was diluted with water (20 ml) and dichloromethane (10 ml), the organic layer was removed, and the remaining aqueous layer extracted with dichloromethane (2×10 ml). The combined organic extracts were combined and washed with brine, then dried ($Na_2SO_4$) and concentrated to an oil which was purified by silica chromatography (15:1 hexanes:ethyl acetate to 10:1 hexanes:ethyl acetate) to give {2-Methyl-4-[3-methyl-1-(4-trifluoromethyl-phenyl)-1H-pyrazol-4-ylmethylsulfanyl]-phenoxy}-acetic acid ethyl ester.

Step B

{2-Methyl-4-[3-methyl-1-(4-trifluoromethyl-phenyl)-1H-pyrazol-4-ylmethylsulfanyl]-phenoxy}-acetic Acid

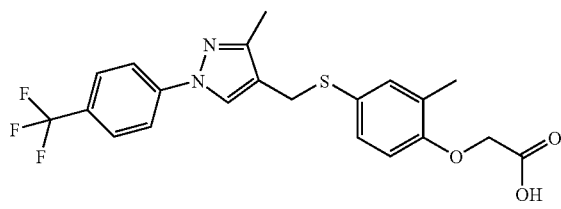

A solution of {2-Methyl-4-[3-methyl-1-(4-trifluoromethyl-phenyl)-1H-pyrazol-4-ylmethylsulfanyl]-phenoxy}-acetic acid ethyl ester (0.27 mmol) in methanol (10 ml) was treated with 5N NaOH (0.54 ml, 2.7 mmol), and the solution was stirred at ambient temperature for 24 hours. The mixture was concentrated to dryness to give a solid which was dissolved in water (10 ml) and ethyl acetate (15 ml), and the solution was then adjusted to pH 3 with 6N HCl. After extraction of the aqueous layer with ethyl acetate (2×15 ml), the organic extracts were combined and washed with water, brine, then dried ($Na_2SO_4$) and concentrated to provide the title compound as a white solid. MS: m/z (M+1) 437. The structure is also confirmed by proton NMR.

BIOLOGICAL ASSAYS

Binding and Cotransfection Studies

The in vitro potency of compounds in modulating PPAR-receptors are determined by the procedures detailed below. DNA-dependent binding is carried out using SPA technology with PPAR receptors. Tritium-labeled PPARα agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPAR agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARδ ("hu" indicates "human"). These studies provide in vitro data concerning efficacy and selectivity of compounds of the invention.

The PPAR transactivation EC50 values for the compound Formula 1 of this invention has been been measured as follows:

PPARα: 1800 nM; PPARγ: 2600 nM PPARδ: 20 nM

Evaluation of Triglyceride Reduction and HDL Cholesterol Elevation in HuapoAI Transgenic Mice A compound of the present invention is studied for effects upon HDL and triglyceride levels in human apoAI mice. Seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1-½ inch curved feeding needle (Popper & Sons). The vehicle for the controls, test compound and the positive control (fenofibrate 100 mg/kg) is 1% carboxymethylcellulose (w/v) with 0.25% tween 80 (w/v). All mice are dosed daily. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured colorimetrically using commercially prepared reagents (for example, as available from Sigma #339-1000 and Roche #450061 for triglycerides and cholesterol, respectively). The procedures are modified from published work (McGowan M. W., et al.; Clin Chem 29:538-542, 1983; Allain C. C., et al.; Clin Chem 20:470-475; 1974. Commercially available standards for triglycerides and total cholesterol, respectively, commercial quality control plasma, and samples are measured in duplicate.

Serum lipoproteins are separated and cholesterol quantitated by fast protein liquid chromatography (FPLC) coupled to an in line detection system.

The percent increase of HDLc serum levels in mice receiving a compound of the invention is compared to mice receiving vehicle.

Efficacy Studies

The compound of Formula 1 was examined in a dyslipidemic rhesus monkey model. An oral dose-escalation study for 28 days in obese, non-diabetic rhesus monkeys demonstrated an elevation of HDL-c with each dose. HDL cholesterol increased by more than 40% in the 3.0 mg/kg b.i.d. dose group. LDL cholesterol decreased by approximately 25% in the 9.0 mg/kg b.i.d dose group, and a dose-related effect on triglycerides yielded a maximum 53% reduction in the 9.0 mg/k.g b.i.d dose group. C-reactive protein levels were reduced compared to pretreatment levels.

Compound of Formula 1 may be shown to elevate plasma HDL-cholesterol levels in an African Green Monkey model in a manner similar to that described above in rhesus monkeys.

Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to measured, for example:

Body weight

Total plasma cholesterol

HDL

LDL

Triglycerides

Insulin

Glucose

PK parameters at week 4, 7, and 10 (plasma drug concentration at last week of each dose)

ApoAI

ApoAII

ApoB

ApoCIII

Liver enzymes (SGPT, SGOT, γGT)

Complete blood count

Additionally, other measures may be made, as appropriate, and consistent with the stated study design.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the Formula I:

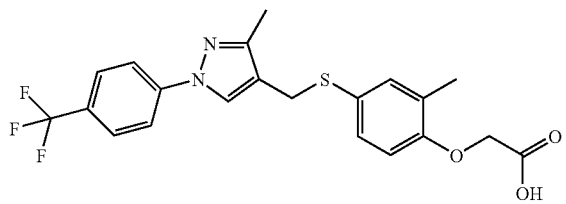

and pharmaceutically acceptable salts, solvates and hydrates thereof.

2. A compound as claimed by claim 1 wherein the compound is {2-Methyl-4-[3-methyl-1-(4-trifluoromethyl-phenyl)-1H-pyrazol-4-ylmethylsulfanyl]-phenoxy}-acetic acid.

3. A pharmaceutical composition, comprising as an active ingredient, at least one compound as claimed by any one of claims 1 and 2 together with a pharmaceutically acceptable carrier or diluent.

4. A method of treating diabetes mellitus in a mammal, comprising the step of administering to the mammal in need thereof a therapeutically effective amount of at least one compound as claimed by any one of claims 1 and 2.

5. A method of claim 4 wherein, the mammal in need of such treatment is diagnosed as needing such treatment by a qualified health care provider.

6. A method of treating Metabolic Syndrome in a mammal, comprising the step of administering to the mammal in need thereof a therapeutically effective amount of at least one compound as claimed by any one of claims 1 and 2.

7. A method of treating atherosclerosis in a mammal, comprising the step of administering to the mammal in need thereof, a therapeutically effective amount of at least one compound as claimed by any one of claims 1 and 2.

8. A compound as claimed by any one of claims 1 and 2 for use as a pharmaceutical.

9. A compound as claimed by any one of claims 1 and 2 wherein the compound is radiolabeled.

* * * * *